(12) United States Patent
Grabis et al.

(10) Patent No.: US 6,322,540 B1
(45) Date of Patent: Nov. 27, 2001

(54) SAFE NEEDLE DEVICE FOR SYRINGE

(75) Inventors: Dietrich W. Grabis, San Rafael; Mary Anne Kaehler, Lodi, both of CA (US); Kenneth Mellberg, St ateline, NV (US)

(73) Assignee: International Technology Group, San Rafael, CA (US)

( * ) Notice: Subject to any disclaimer, the term of this patent is extended or adjusted under 35 U.S.C. 154(b) by 0 days.

(21) Appl. No.: 09/524,144

(22) Filed: Mar. 10, 2000

(51) Int. Cl.⁷ .................................................. A61M 5/32
(52) U.S. Cl. ............................................. 604/198; 604/110
(58) Field of Search .................................. 604/110, 198, 604/263, 192, 195, 218, 220, 221, 228

(56) References Cited

U.S. PATENT DOCUMENTS

| | | | |
|---|---|---|---|
| 3,880,163 | * | 4/1975 | Rikkerskamp ........................ 604/136 |
| 5,147,303 | * | 9/1992 | Martin .................................. 604/110 |
| 5,279,582 | * | 1/1994 | Davison et al. ...................... 604/198 |
| 5,411,487 | * | 5/1995 | Castagna ............................. 604/198 |
| 5,591,138 | * | 1/1997 | Vaillancourt ..................... 604/198 X |
| 5,885,257 | | 3/1999 | Badger . |

* cited by examiner

Primary Examiner—Anhtuan T. Nguyen
(74) Attorney, Agent, or Firm—Flehr Hohbach Test Albritton & Herbert LLP

(57) ABSTRACT

A needle stick safety syringe includes a outer tubular protective cover or sleeve for the inner syringe body where a concentric coil spring is compressed against the normal flange of the inner syringe body and retained there by a stop which is cantilevered from a collar affixed to the distal end of the inner syringe body. This cantilevered stop also includes a convenient button which may be easily depressed by a finger of one hand holding the outer tubular body to allow the sleeve to be slid over the needle under the bias of the spring. The cantilevered button and stop rides in a groove in the inner diameter of the tubular outer protective body and is captured by a slot which effectively prevents reuse.

6 Claims, 3 Drawing Sheets

SAFE NEEDLE DEVICE FOR SYRINGE

INTRODUCTION

The present invention is directed in general to a safe needle device for syringes as used in the medical industry and hospitals.

BACKGROUND OF THE INVENTION

With the advent of AIDS and other highly infectious diseases, syringes and scalpels and other sharp devices have caused numerous injuries and infections to the administering medical staff. Legislation has been enacted, including California (State of California Labor Code §144.7(d)) requiring some type of protection to the medical staff.

Protective devices have been proposed, but these devices have been scattered and non-functional and are not user-friendly. For example, a nurse must use two hands to prepare a patient for an injection. One hand is used to clean the area to be injected with a disinfectant while the other hand is used to inject the needle into the tissue. After removing the needle from the patient, the administering nurse must press on to the spot of injection and hold the syringe in the other hand. After pressing the spot of injection is completed (to stop the flow of blood), the nurse, in prior protective devices, then uses that hand to twist a cover over the syringe or sharp That requires two hands during which time the needle may drip blood onto the patient or the nurse where contamination is inevitable. In addition, the maneuvering to accomplish the foregoing may cause an inadvertent puncturing of the nurse's own skin, thus inviting infection. One such device requiring a two-handed operation is Badger U.S. Pat. No. 5,885,257, which is a very cumbersome releasable retaining device to retract the needle syringe where it will not cause harm.

OBJECT AND SUMMARY OF THE INVENTION

It is a general object of this invention to provide an improved safe needle device for syringes.

In accordance with the above object, there is provided a needle-stick safety syringe comprising an inner tubular body, plunger, and extended needle at the distal end of the tubular body. A larger protective tubular body is concentric with the inner tubular body and freely slidable thereon. Spring means between the proximal ends of the tubular bodies bias them apart. Latch means oppose the biasing including a collar with a flexible cantilevered stop, such collar being permanently fixed to the distal end of the inner tubular body and having an outer diameter which freely slides within the protective tubular body. The stop hooks against a distal edge of the protective tubular body whereby the bias of the spring means is opposed. Slot means in the protective tubular body near its proximal end receive and capture the stop when pushed by a finger of a hand grasping said protective tubular body.

In addition, a method is provided of constructing a needle stick safety syringe having an inner tubular body terminating in a flange at its proximal end, a plunger, and extended needle at its distal end comprising the following steps. A larger concentric protective tubular body is provided which slides over the inner tubular body of the syringe. The proximal end of the larger tubular body is plugged serving as an abutment holding a coil spring against the flange. A collar is provided with a flexible cantilevered stop and an inner diameter capable of being permanently affixed to the distal end of the syringe body. The collar has an outer diameter which will freely slide in the protective tubular body. The coil spring is placed on the syringe tube, the plug and subsequently the protective tubular body is slid against the spring bias and the stop is affixed until the cantilevered stop hooks against a distal end of the protective tubular body, whereby pushing the stop allows it to ride against the inside of the protective tubular body which then covers the exposed needle due to the expansion of the coil spring. A slot is provided in the proximal end of the protective tubular body in which the stop is captured thereby limiting expansion of said spring and movement of the protective tube under the bias of the expanding coil spring.

DETAILED DESCRIPTION OF THE PREFERRED EMBODIMENT

Figure 1:
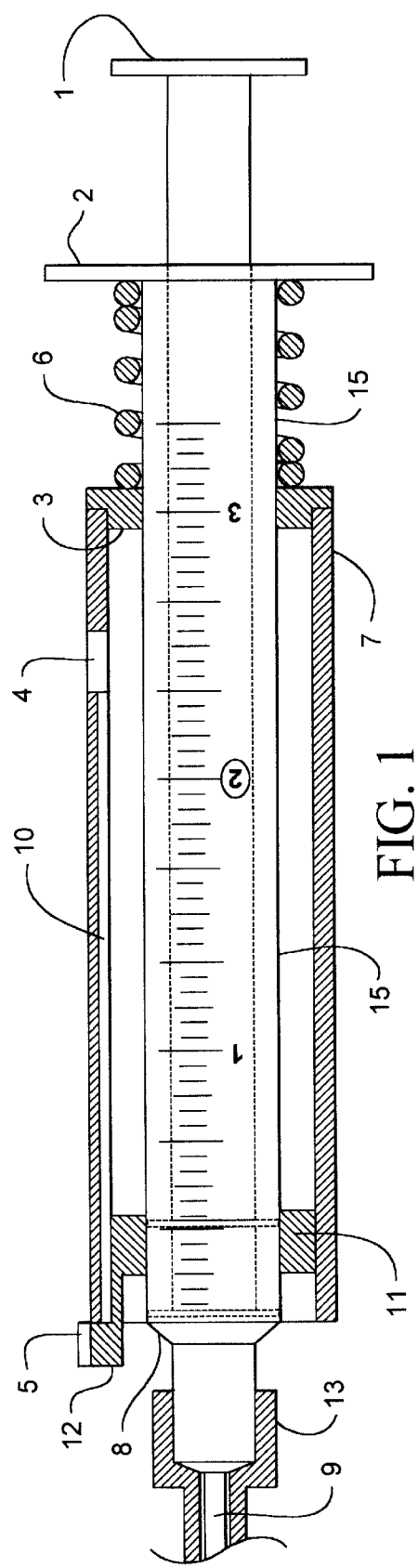
FIG. 1 is a cross-sectional view of a syringe embodying the present invention showing its unreleased condition.

Referring now to FIG. 1, a typical commercial syringe of the so-called "TB" type, that is with a 3cc capacity and is illustrated with an inner tubular body 15, a plunger 1 that slides within the tubular body operates in the standard manner. The inner tubular body 15 has a flange 2 at its proximal end and an extended needle 9 at its distal end 8 with a protective cover 13.

Figure 4:
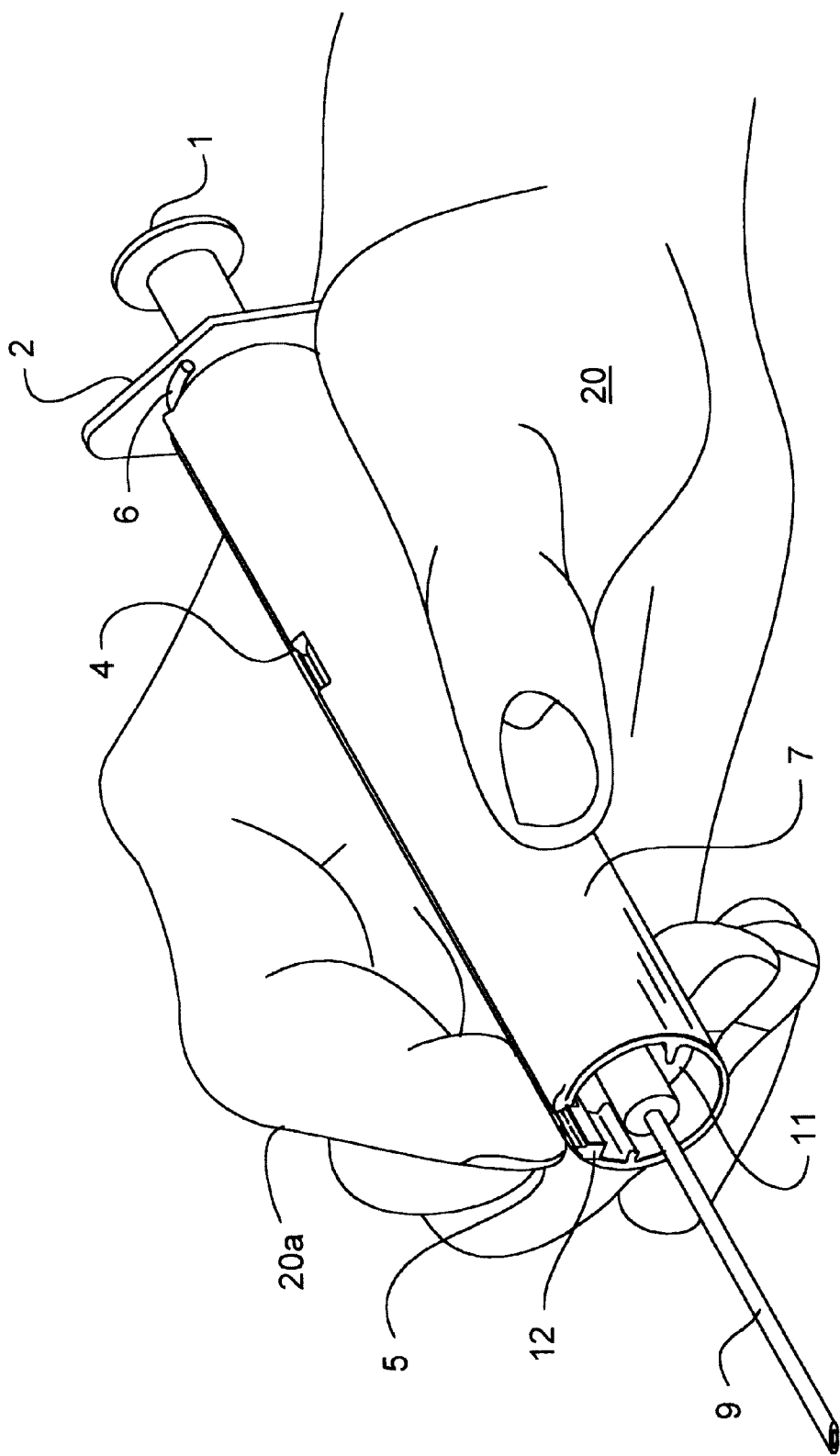
FIG. 4 is a perspective view showing how the syringe is used by medical personnel.

At that distal end 8 in accordance with the technique of the present invention, there is provided a collar 11 which is permanently or friction fitted or affixed onto tube 15 at the distal end and which carries a cantilevered stop 12 (which is flexible) having a button-type termination 5 which is easily engageable by a human hand 20 (see FIG. 4).

A larger concentric protective sleeve type tubular body 7 (having a diameter larger than the inner syringe body 15) is slidable over the syringe body as illustrated in FIG. 1, and includes at its distal end a plug 3. Syringe body 15 is freely slidable within that plug. A coil spring 6 is initially slid on the inner tubular body 15 and abuts against the flange 2 at one end with the other end being retained by the abutment plug 3. The cantilevered stop 12 with its button 5 in this unreleased condition retains the spring 6 in a compressed condition because of the cantilevered stop 12 hooking against the proximal edge of the tube 7.

Thus, in actual construction, spring 6 would be slid onto the syringe tube. Thereafter the plug 3 is slid against the spring, then the outer protective sleeve 7 is slid on the syringe tube and mates with plug 3. Finally the collar 11 would be permanently affixed, for example, by friction fitting or even glueing.

Figure 2:
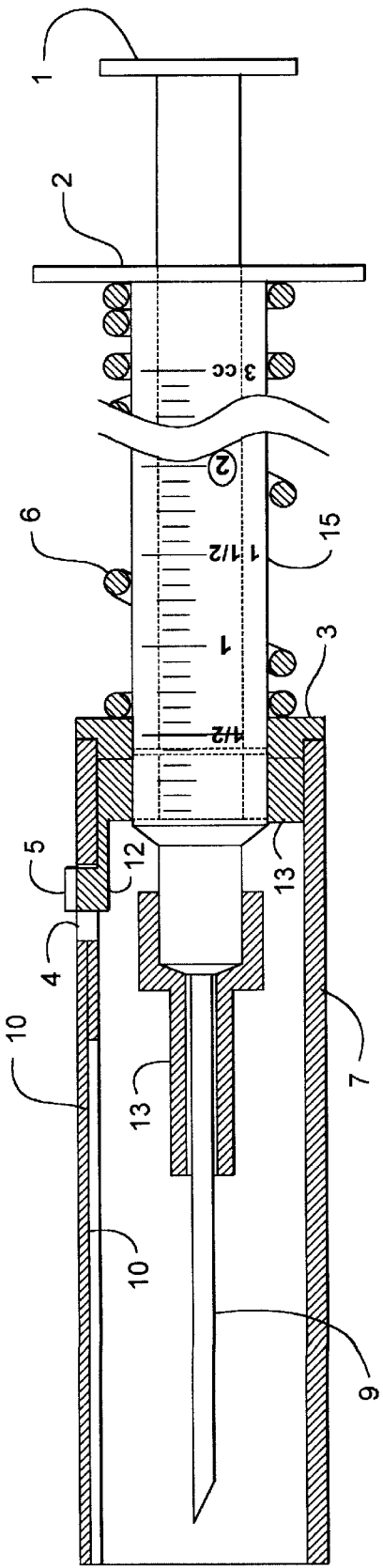
FIG. 2 is a cross-sectional view similar to FIG. 1 showing a released condition where the needle is protected by an outer tubular body.
Figure 3:
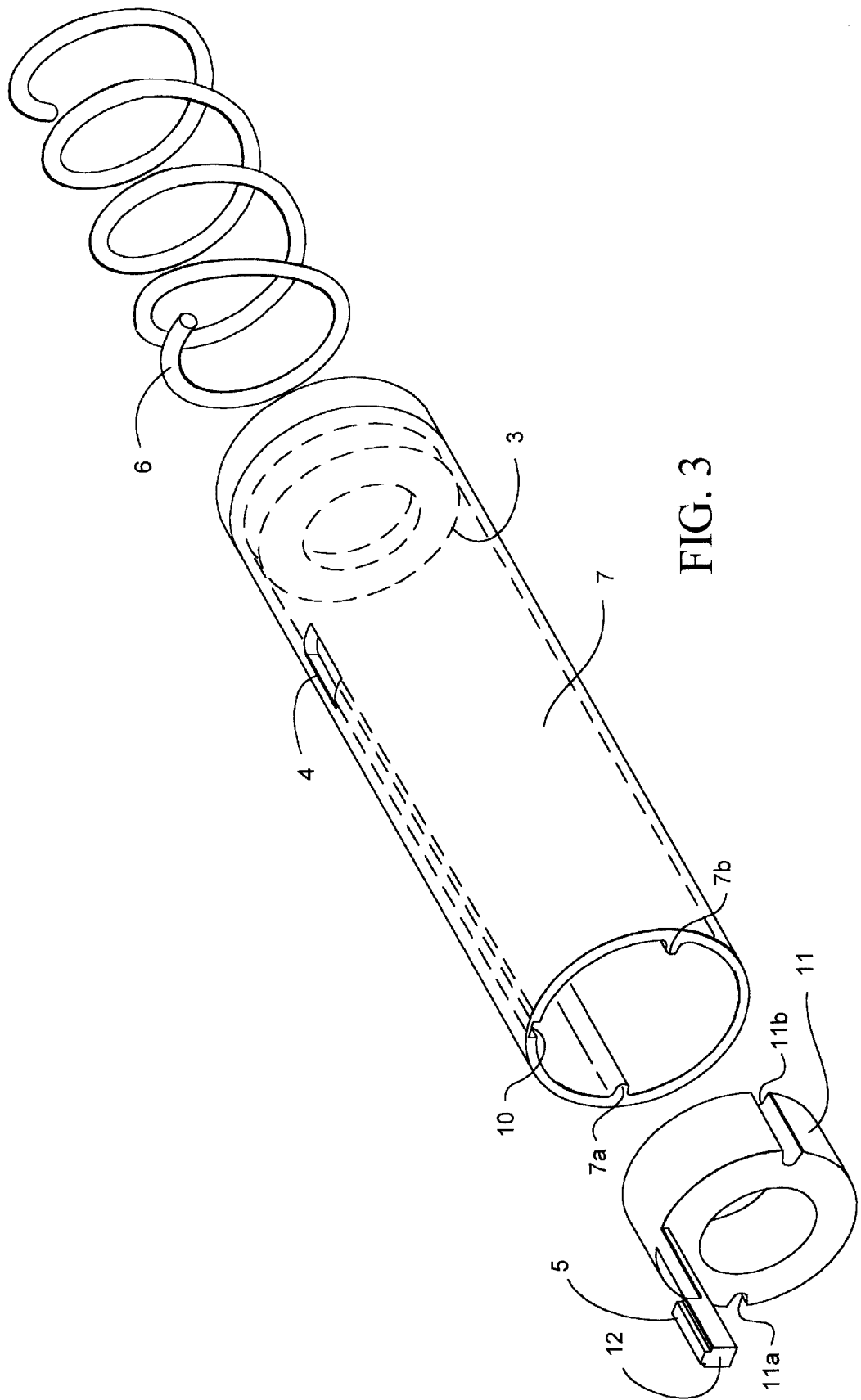
FIG. 3 is an exploded perspective view showing a portion of FIGS. 1 and 2.

FIG. 3 shows further details of the invention where the spring 6 is illustrated along with the abutment plug 3 where the outer protective tubular body 7 includes an interior groove 10 which will guide the stop 12 (when depressed by a human finger) to a slot 4 in the proximal end of tubular body 7. To further prevent twisting and enhance the travel of the collar 11, the collar includes a pair of grooves 11a, 11b diametrically opposed which mate with a similar pair of axial guides 7a and 7b on the interior of tubular body 7. As discussed above, the outer diameter of collar 11 is freely slidable within tubular body 7 but its inner diameter is friction fitted or permanently affixed to the inner tubular body of the syringe 15. After an injection has been made on the patient, the needle 9 is withdrawn as illustrated in FIG. 4 and held in one hand 20 by the nurse or medical person. The other hand, of course, would be used to press the spot of injection. Then with a suitable finger such as the index finger 20a, button 5 on cantilever 12 is pressed. As illustrated in FIG. 2, this releases tube 15 and allows the force of the spring to relatively move the outer protective tubular body 7 to cover the needle 9. As this is occurring in the channel 10 the button 5 and its cantilevered end 12 have moved and are captured by the slot 4.

This process, as is apparent from FIG. 2, is not reversible and there is no way to effectively depress button 5 to again expose needle 9. Thus, ultimate safety is provided. This syringe is then disposed of by the administering nurse or physician.

Protective cover 7 may be fabricated of plastic or glass to provide transparency for viewing the contents of the syringe and the gradations as illustrated in FIG. 1.

Thus in summary, the present invention provides an improved needle stick safety syringe that does not require the use of a second hand when withdrawal or removal takes place. It is easily handled by unskilled persons without special tools or skills or instructions. Moreover, the outer protective body or sleeve 7 is constructed in such a way that it cannot rotate or twist during the retraction mode. This action provides for linear alignment and straight retrieval of the needle into the sleeve directly into the locking slot.

What is claimed is:

1. A needle-stick safety syringe comprising:
    an inner tubular body, plunger, and extended needle at the distal end of the tubular body;
    a larger protective tubular body concentric with said inner tubular body freely slidable thereon;
    spring means between the proximal ends of said tubular bodies for biasing them apart;
    latch means for opposing said biasing including a collar with a flexible cantilevered stop, such collar being permanently fixed to the distal end of said inner tubular body and having an outer diameter which freely slides within said protective tubular body, said stop hooking against a distal edge of said protective tubular body whereby the bias of said spring means is opposed;
    slot means in said protective tubular body near its proximal end for receiving and capturing said stop when pushed by a finger of a hand grasping said protective tubular body.

2. A needle stick safety syringe as in claim 1 where said latch means includes an interior groove in said protective body to guide said stop to said slot means.

3. A needle stick safety syringe as in claim 1 where said spring means is a coil spring concentric with said inner and protective tubular bodies.

4. A method of constructing a needle stick safety syringe having an inner tubular body terminating in a flange at its proximal end, a plunger, and extended needle at its distal end comprising the following steps:
    providing a larger concentric protective tubular body which slides over said inner tubular body of said syringe;
    providing a plug for the proximal end of said larger tubular body serving as an abutment holding a coil spring against said flange;
    providing a collar with a flexible cantilevered stop and an inner diameter capable of being permanently affixed to the distal end of said syringe body, the collar having an outer diameter which will freely slide in said protective tubular body;
    placing said coil spring on the syringe tube, sliding on said plug and subsequently the protective tubular body against the spring bias, and affixing said stop until the cantilevered stop hooks against a distal end of said protective tubular body;
    whereby pushing said stop allows it to ride against the inside of the protective tubular body which then covers the exposed needle due to the expansion of the coil spring;
    and providing a slot in the proximal end of said protective tubular body in which said stop is captured thereby limiting expansion of said spring and movement of said protective tube under the bias of said expanding coil spring.

5. A needle stick syringe as in claim 1 where said protective tubular body is graspable by a single human hand between the thumb and selected fingers with one of such fingers of such grasping hand being able to push said stop to allow said coil spring means to expand to cover said extended needle with said protective tubular body.

6. A needle stick safety syringe as in claim 1 where said protective tubular body includes a pair of axial guides on the inner diameter of such body for mating with a pair of grooves on said collar for preventing twisting when said stop is released and said collar slides within said protective tubular body carrying said inner tubular body of said syringe.

* * * * *